United States Patent [19]

Wentland et al.

[11] Patent Number: 4,517,191

[45] Date of Patent: May 14, 1985

[54] 1-AMINO-1,8-NAPHTHYRIDINE COMPOUNDS USEFUL AS BACTERICIDES

[75] Inventors: Mark P. Wentland, North Greenbush; Denis M. Bailey, East Greenbush, both of N.Y.

[73] Assignee: Sterling Drug Inc., New York, N.Y.

[21] Appl. No.: 537,195

[22] Filed: Sep. 29, 1983

[51] Int. Cl.³ .................. A61K 31/44; C07D 471/04
[52] U.S. Cl. ..................... 514/300; 546/123
[58] Field of Search .................. 546/123; 424/256

[56] References Cited

U.S. PATENT DOCUMENTS 3,590,036 6/1971 Lesher et al. .................. 424/248
4,284,629 8/1981 Grohe et al. .................. 424/286

OTHER PUBLICATIONS

Wagner and Zook, Synthetic Org. Chem., (1953), pp. 678–679.
Blicke et al., J.A.C.S. (1946), vol. 68, pp. 905–906.

*Primary Examiner*—Henry R. Jiles
*Assistant Examiner*—Bernard I. Dentz
*Attorney, Agent, or Firm*—Thomas L. Johnson; B. Woodrow Wyatt; Paul E. Dupont

[57] ABSTRACT

Compounds of the formula

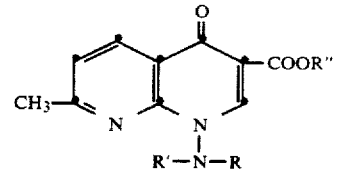

wherein R is hydrogen or formyl; and R' and R" are hydrogen or lower-alkyl, are useful as antibacterial agents or as intermediates, and are prepared from the corresponding compounds unsubstituted in the 1-position.

12 Claims, No Drawings

1-AMINO-1,8-NAPHTHYRIDINE COMPOUNDS USEFUL AS BACTERICIDES

BACKGROUND OF THE INVENTION

1. Field of the Invention

The present invention relates to novel naphthyridine compounds, useful as antibacterial agents or as intermediates.

2. Information Disclosure Statement

Certain substituted 1,4-dihydro-4-oxo-1,8-naphthyridine-3-carboxylic acids are known to possess antibacterial activity. Lesher and Gruett U.S. Pat. No. 3,590,036, issued June 29, 1971, describes such acids wherein the 1-position bears an optionally substituted hydrocarbon group. Illustrative of the compounds disclosed are 1-ethyl-1,4-dihydro-7-methyl-4-oxo-1,8-naphthyridine-3-carboxylic acid (nalidixic acid) (Example 1) and 1-(2-diethylaminoethyl)-1,4-dihydro-7-methyl-4-oxo-1,8-naphthyridine-3-carboxylic acid (Example 30).

Grohe et al. U.S. Pat. No. 4,284,629, issued Aug. 18, 1981, discloses certain bicyclic 1,4-dihydro-4-pyridone-3-carboxylic acids substituted in the 1-position, inter alia, by a tertiary-amino group. Exemplary of the compounds disclosed are 1-dimethylamino-6-nitro-2-methyl-1,4-dihydro-4-oxoquinoline-3-carboxylic acid, methyl ester (Example 4), and 1-(4-morpholinyl)-2,7-dimethyl-1,4-dihydro-4-oxo-1,8-naphthyridine-3-carboxylic acid (Example 23).

SUMMARY OF THE INVENTION

In a product aspect, the invention relates to new chemical compounds of the formula

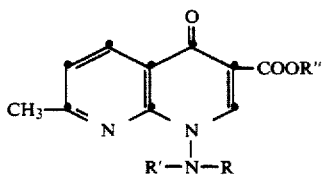

I wherein R is hydrogen or formyl; and R' and R" are hydrogen or lower-alkyl; or alkali metal or pharmaceutically acceptable amine salts of compounds where R" is hydrogen.

In a further product aspect, the invention relates to antibacterial compositions containing compounds of Formula I where R and R" are hydrogen and R' is lower-alkyl.

In a process aspect, the invention relates to a process for preparing a compound of the formula

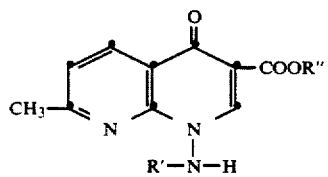

wherein R' is lower-alkyl and R" is hydrogen or lower-alkyl; or an alkali metal salt thereof, which comprises:

(a) alkylating a compound of the formula

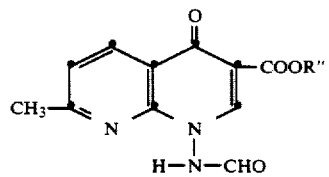

wherein R" has the meaning given above, with a lower-alkyl halide, R'X, where X is Br or I, in the presence of a base to give a compound of the formula

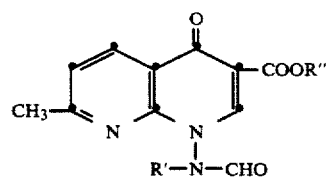

where R' and R" are lower-alkyl;

(b) subjecting the resulting compound to alkaline hydrolysis; and (c) if desired, converting the resulting alkali metal salt of the product to the free acid where R" is hydrogen.

In a further process aspect, the invention relates method for combatting bacteria with compositions containing compounds of Formula I where R and R" are hydrogen, and R' is lower-alkyl.

DETAILED DESCRIPTION INCLUSIVE OF PREFERRED EMBODIMENTS

In the definition of the variables in Formula I above, the term "lower-alkyl" stands for alkyl preferably having from one to three carbon atoms, thus including methyl, ethyl, propyl and isopropyl.

The compounds of the invention are prepared starting from the known compounds (U.S. Pat. No. 3,590,036) of the formula

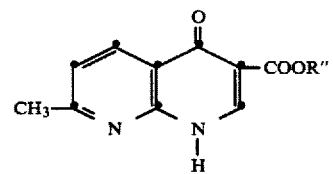

where R" is hydrogen or lower-alkyl, in accordance with the following flow-sheet:

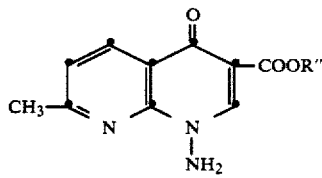

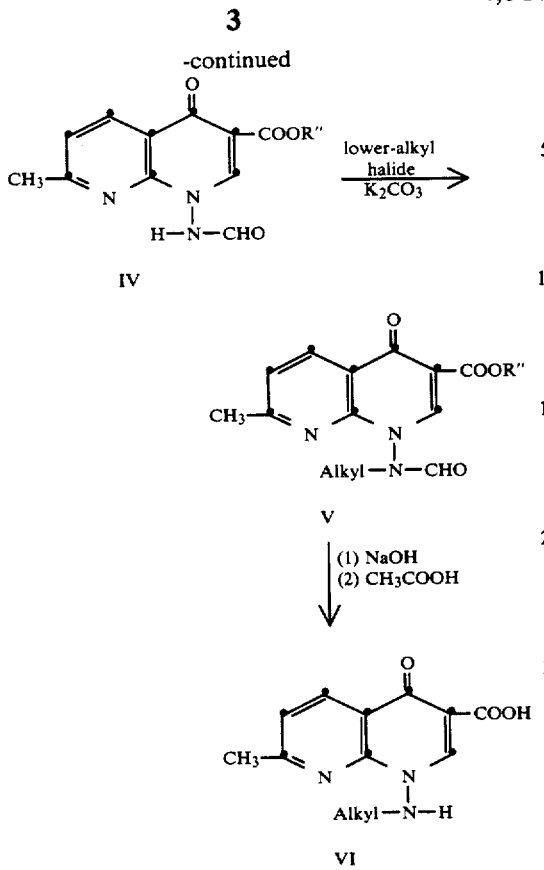

The amino function is introduced into the 1-position of the 1,8-naphthyridine nucleus by treatment of a known starting material of Formula II with an aminating agent, e.g. chloramine or an O-arylhydroxylamine such as O-(2,4-dinitrophenyl)hydroxylamine [2,4-$(O_2N)_2C_6H_3ONH_2$]; cf. Tamura et al., J. Org. Chem. 38, 1239 (1973). This results in a compound of Formula III. The reaction takes place at ambient temperature in an inert organic solvent in the presence of a base such as potassium carbonate.

A compound of Formula III is then formylated with a mixture of formic acid and acetic anhydride to give an N-formyl derivative (IV). The latter is then alkylated with a lower-alkyl halide, preferably the iodide or bromide, in the presence of a base such as potassium carbonate to afford an N-lower-alkyl-N-formyl compound (V). Hydrolysis of the latter with a base such as sodium hydroxide and acidification of the reaction mixture yields an N-loweralkylcarboxylic acid of Formula VI (I; R and R″=H, R′=alkyl).

Esters of Formula I where R is hydrogen and R′ and R″ are alkyl can be prepared by selective hydrolysis of compounds of Formula V (R″=alkyl) whereby the formyl group is removed and the ester group retained intact. Alternatively said ester of Formula I can be prepared by conventional esterification of the corresponding acids (R″=H).

The compounds of Formula I where R″ is hydrogen can also be prepared and used in the form of their alkali metal or pharmaceutically acceptable amine salts, preferably the sodium, potassium, N-methylglucamine or diethanolamine salts.

The following examples will further illustrate the invention.

EXAMPLE 1

Ethyl 1-amino-1,4-dihydro-7-methyl-4-oxo-1,8-naphthyridine-3-carboxylate [III; R″=$C_2H_5$]

A mixture of 9.7 g (0.0417 m) of ethyl 1,4-dihydro-7-methyl-4-oxo-1,8-naphthyridine-3-carboxylate, 11.5 g (0.0834 m) of potassium carbonate and 200 ml of dimethylformamide was slurried at room temperature, and 8.3 g (0.0417 m) of O-(2,4-dinitrophenyl)hydroxylamine was added. The reaction mixture was stirred for 17 hours and then concentrated in vacuo. The residue was dissolved in 1 liter of warm water and extracted with 800 ml of chloroform. The extracts were filtered, dried over anhydrous magnesium sulfate, decolorized with charcoal and concentrated in vacuo. The residue was recrystallized from ethanol and chromatographed on silica gel, using isopropyl alcohol-chloroform (1:9) for elution, to give 6.5 g of ethyl 1-amino-1,4-dihydro-7-methyl-4-oxo-1,8-naphthyridine-3-carboxylate, buff-colored solid, m.p. 173°–174° C. when recrystallized from ethanol.

EXAMPLE 2

1-Amino-1,4-dihydro-7-methyl-4-oxo-1,8-naphthyridine-3-carboxylic acid [III; R″=H]

A mixture of 10.0 g (0.0405 m) of ethyl 1-amino-1,4-dihydro-7-methyl-4-oxo-1,8-naphthyridine-3-carboxylate, 1.94 g (0.0486 m) of sodium hydroxide and 350 ml of water was heated on a steam bath for two hours. The resulting solution was filtered, cooled and neutralized with 3 ml of acetic acid while stirring. The solid product was collected by filtration, washed with water and recrystallized by dissolving it in 100 ml of boiling dimethylformamide and adding 100 ml of ether to the cooled solution. There was obtained 7.8 g of 1-amino-1,4-dihydro-7-methyl-4-oxo-1,8naphthyridine-3-carboxylic acid, colorless needles, m.p. 239°–240° C.

EXAMPLE 3

Ethyl 1-(formylamino)-1,4-dihydro-7-methyl-4-oxo-1,8-naphthyridine-3-carboxylate [IV; R″=$C_2H_5$]

Formic acid (13 ml, 0.33 m) was added to 31.2 ml (0.33 m) of acetic acid stirred in an ice bath. The mixture was stirred 15 minutes at 0° C. and 15 minutes at 55° C. It was then recooled to 0° C. and 8.1 g (0.033 m) of ethyl 1-amino-1,4-dihydro-7-methyl-4-oxo-1,8-naphthyridine-3-carboxylate was added. An additional 9.2 ml of formic acid was then added, and the reaction mixture was stirred one hour at 0° C. and two hours at room temperature. The reaction mixture was poured into ice-water, and the solid product collected by filtration, washed with water, tetrahydrofuran and ether, and dried at 75° C. in vacuo to give 4.4 g of ethyl 1-(formylamino)-1,4-dihydro-7-methyl-4-oxo-1,8-naphthyridine-3-carboxylate, m.p. 214° C. (decompn), which contained a minor amount of the corresponding N,N-diformyl compound.

EXAMPLE 4

Ethyl 1-(N-formylmethylamino)-1,4-dihydro-7-methyl-4-oxo-1,8-naphthyridine-3-carboxylate [V; R″=C$_2$H$_5$, Alkyl=CH$_3$]

Ethyl 1-(formylamino)-1,4-dihydro-7-methyl-4-oxo-1,8-naphthyridine-3-carboxylate (11.8 g, 0.043 m) was added to a stirred mixture of 20.3 g (0.136 m) of anhydrous, milled potassium carbonate and 103 ml of dimethylformamide. The mixture was stirred for 30 minutes, and 20.3 ml (0.33 m) of methyl iodide was then added. The reaction mixture was stirred for five hours on a steam bath, then at room temperature overnight, and poured into 400 ml of ice-water. The solid product was collected by filtration, washed with water, and dried at 60° C. in vacuo to give 8.1 g of ethyl 1-(N-formylmethylamino)-1,4-dihydro-7-methyl-4-oxo-1,8-naphthyridine-3-carboxylate, beige solid, m.p. 210°-212° C.

It is contemplated that by replacing the methyl iodide in the foregoing preparation by a molar equivalent amount of propyl iodide, there can be obtained ethyl 1-(N-formylpropylamino)-1,4-dihydro-7-methyl-4-oxo-1,8-naphthyridine-3-carboxylate [V; R″=C$_2$H$_5$, Alkyl=CH$_3$CH$_2$CH$_2$].

EXAMPLE 5

1,4-Dihydro-7-methyl-1-methylamino-4-oxo-1,8-naphthyridine-3-carboxylic acid [VI; Alkyl=CH$_3$]

A solution of 85% potassium hydroxide (2.25 g, 0.035 m) in 7.8 ml of water was added to a refluxing solution of 4.5 g (0.016 m) of ethyl 1-(N-formylmethylamino)-1,4-dihydro-7-methyl-4-oxo-1,8-naphthyridine-3-carboxylate in 141 ml of absolute ethanol. The reaction mixture was heated at reflux for one hour, then allowed to stand at room temperature for three days, and poured into 100 ml of ice-water and filtered. The filtrate while cold was acidified with acetic acid, and the solid product was collected by filtration, washed with water and dried at 50° C. in vacuo to yield 3.3 g of 1,4-dihydro-7-methyl-1-methylamino-4-oxo-1,8-naphthyridine-3-carboxylic acid, beige solid, m.p. 215°-217° C.

It is contemplated that by using milder hydrolytic conditions, e.g. a temperature of 60° C. instead of 100° C. there can be obtained ethyl 1,4-dihydro-7-methyl-1-methylamino-4-oxo-1,8-naphthyridine-3-carboxylate [I; R′=H, R′=CH$_3$, R″=C$_2$H$_5$].

EXAMPLE 6

Ethyl 1-(N-formylethylamino)-1,4-dihydro-7-methyl-4-oxo-1,8-naphthyridine-3-carboxylate [V; R″=C$_2$H$_5$, Alkyl=C$_2$H$_5$] was prepared from ethyl 1-(formylamino)-1,4-dihydro-7-methyl-4-oxo-1,8-naphthyridine-3-carboxylate and ethyl iodide, following the procedure of Example 4, and was obtained in the form of a tan solid, m.p. 175°-178° C.

EXAMPLE 7

1-Ethylamino-1,4-dihydro-7-methyl-4-oxo-1,8-naphthyridine-3-carboxylic acid [VI; Alkyl=C$_2$H$_5$] was prepared by hydrolysis of ethyl 1-(N-formylethylamino)-1,4-dihydro-7-methyl-4-oxo-1,8-naphthyridine-3-carboxylate according to the procedure of Example 5, and was obtained in the form of a tan solid, m.p. 166°-169° C.

Similarly it is contemplated that ethyl 1-(N-formylpropylamino)-1,4-dihydro-7-methyl-4-oxo-1,8-naphthyridine-3-carboxylate can be hydrolyzed to 1,4-dihydro-7-methyl-4-oxo-1-propylamino-1,8-naphthyridine-3-carboxylic acid [VI; Alkyl=CH$_2$CH$_2$CH$_3$].

The in vitro antibacterial activity of the compounds of the invention was determined by conventional serial dilution procedures. Bacterial cultures were grown in tryptose phosphate broth or brain heart infusion broth (containing heat-inactivated normal horse serum for tests with *S. pyogenes*) overnight at 37° C. and subsequently diluted in double strength broth to provide bacterial inocula of about $2 \times 10^5$ cells/ml. Aqueous solutions of the compounds of Formula I where R″ is hydrogen were prepared by dissolving the free acid form in 0.5N sodium hydroxide. The solutions were diluted with sterile distilled water to 1000 mcg/ml of compound in terms of the free acid. Serial two-fold dilutions of the compound stock solutions were prepared in water and 0.5 ml of each dilution was transferred to sets of tubes, one set for each bacterial inoculum. Each tube was then inoculated with 0.5 ml of the appropriate culture, resulting in a final bacterial concentration of about $1 \times 10^5$ cells/ml. The minimal inhibitory concentration (MIC), defined as the lowest concentration of the test compound to inhibit visible bacterial growth, was recorded after 18-20 hours of static incubation at 37° C. The results are recorded in Table I:

TABLE I

| | Minimal Inhibitory Concentration (mcg/ml) | |
|---|---|---|
| | Compound Example No. | |
| Bacteria | 5 | 7 |
| *Staphylococcus aureus* Smith | >500 | >500 |
| *Streptococcus pyogenes* C203 | >500 | >500 |
| *Escherichia coli* Vogel | 31.3 | 31.3 |
| *Klebsiella pneumoniae* 39645 | 62.5 | 125 |
| *Proteus mirabilis* MGH-1 | 62.5 | 250 |
| *Proteus vulgaris* 9920 | 62.5 | 15.6 |
| *Pseudomonas aeruginosa* MGH-2 | >500 | >500 |

The compounds of Examples 1, 2, 4 and 6 were inactive at the highest concentrations tested (62.5-500 mcg/ml). These are intermediates for the compounds of Examples 5 and 7.

The in vivo antibacterial activity of the compounds of the invention was determined in female mice, 18-20 grams each, by the following procedure:

Aqueous solutions of the compounds of Formula I where R″ is hydrogen were prepared by dissolving the free acid form in dilute sodium hydroxide and diluting the solution with distilled water to the desired volume.

Cultures of *Escherichia coli* Vogel prepared in brain heart infusion broth, and cultures of *Klebsiella pneumoniae* 39645 grown in tryptose phosphate broth with 5% rabbit serum diluted in the same broth were used to infect the mice as follows:

*E coli:* mice were inoculated intraperitoneally with 0.5 ml of the bacerial test inoculum ($1.87 \times 10^7$ and $5 \times 10^6$ cells/ml respectively).

*K. pneumoniae:* mice were inoculated intramuscularly in the right hind leg with 0.2 ml of the bacterial test inoculum ($2.05 \times 10^4$ cells/ml).

Mice infected with *E. coli* were medicated once (0.5 ml) one-half hour post infection, the test compound being administered by the subcutaneous (s.c.) route. Deaths were recorded daily for seven days.

Mice infected with *K. pneumoniae* were medicated at the following times: seventeen hours and one hour preinfection, six hours postinfection and twice a day for the next three days. The test compound was administered the subcutaneous (0.2 ml) route. Deaths were recorded daily for fourteen days.

Groups of ten animals each for four or five dose levels were thus treated and the number of survivors in each group recorded. The fifty percent protective dose values (PD$_{50}$) were then calculated. The results obtained are given in Table II:

TABLE II

| Protective Dose (PD$_{50}$, mg/kg s.c.) | | |
|---|---|---|
| Compound Example No. | *E. coli* | *K. pneumoniae* |
| 5 | 141 | >200 |
| 6 | 53.5 | >200 |
| 7 | 93 | >200 |

The compounds of the invention which are active in vitro can be used for topical application and for disinfection of inanimate objects.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

We claim:

1. A compound having the formula

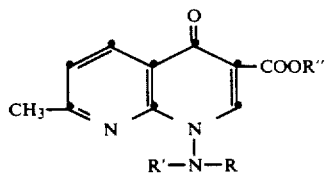

wherein R is hydrogen or formyl; and R' and R" are hydrogen or lower-alkyl; or an alkali metal or pharmaceutically acceptable amine salt of a compound where R" is hydrogen.

2. A compound according to claim 1 wherein R and R" are hydrogen and R' is lower-alkyl.

3. 1,4-Dihydro-7-methyl-1-methylamino-4-oxo-1,8-naphthyridine-3-carboxylic acid, according to claim 2.

4. 1-Ethylamino-1,4-dihydro-7-methyl-4-oxo-1,8-naphthyridine-3-carboxylic acid, according to claim 2.

5. A compound according to claim 1 wherein R and R' are both hydrogen.

6. Ethyl 1-amino-1,4-dihydro-7-methyl-4-oxo-1,8-naphthyridine-3-carboxylate, according to claim 5.

7. 1-Amino-1,4-dihydro-7-methyl-4-oxo-1,8-naphthyridine-3-carboxylic acid, according to claim 5.

8. A compound according to claim 1 wherein R is formyl and R" is lower-alkyl.

9. Ethyl 1-(N-formylmethylamino)-1,4-dihydro-7-methyl-4-oxo-1,8-naphthyridine-3-carboxylate, according to claim 8.

10. Ethyl 1-(N-formylethylamino)-1,4-dihydro-7-methyl-4-oxo-1,8-naphthyridine-3-carboxylate, according to claim 8.

11. A composition for combatting bacteria, which comprises an antibacterially effective amount of a compound according to claim 2 together with one or more pharmaceutically acceptable excipients.

12. A method for combatting bacteria, which comprises contacting the locus of said bacteria with a composition according to claim 11.

* * * * *

UNITED STATES PATENT AND TRADEMARK OFFICE
CERTIFICATE OF CORRECTION

PATENT NO. : 4,517,191

DATED : May 14, 1985

INVENTOR(S) : Mark P. Wentland & Denis M. Bailey

It is certified that error appears in the above-identified patent and that said Letters Patent is hereby corrected as shown below:

Column 2, line 29, insert "to a" before --method--.

Column 3, line 37, "O-aryl..." should read --O-aryl...--.

Column 5, line 48, "R' = H" should read --R = H--.

Signed and Sealed this

Seventeenth Day of September 1985

[SEAL]

Attest:

DONALD J. QUIGG

Attesting Officer

Commissioner of Patents and
Trademarks—Designate